United States Patent [19]

Kan et al.

[11] Patent Number: 4,859,488

[45] Date of Patent: Aug. 22, 1989

[54] LIQUID FOOD FOR CURING CONSTIPATION: POLYDEXTROSE AND OLIGOSACCHARIDE

[75] Inventors: Tatsuhiko Kan; Yoichi Kobayashi; Yoshiko Sonoike; Tsuneo Terashima; Masahiko Mutai, all of Tokyo, Japan

[73] Assignee: Kabushiki Kaisha Yakult Honsha, Tokyo, Japan

[21] Appl. No.: 96,483

[22] Filed: Sep. 15, 1987

[51] Int. Cl.$^4$ .................. A23L 1/30; A61K 31/17

[52] U.S. Cl. .................. 426/658; 426/531; 426/615; 536/1.1; 536/114; 536/123

[58] Field of Search .................. 426/658; 536/1.1, 123

[56] References Cited

U.S. PATENT DOCUMENTS 3,766,165 10/1973 Rennhard .................. 536/1.1
4,024,290 5/1977 Layton .................. 536/12 D
4,435,389 3/1984 Mutai et al. .................. 428/181

FOREIGN PATENT DOCUMENTS 57-018982 1/1982 Japan .
58-099497 6/1983 Japan .
58-099498 6/1983 Japan .
58-201980 11/1983 Japan .
58-212780 12/1983 Japan .
59-011190 1/1984 Japan .
59-039287 3/1984 Japan .
59-053835 3/1984 Japan .
59-173062 9/1984 Japan .
59-179064 10/1984 Japan .

OTHER PUBLICATIONS

"Epidemiology of Cancer of the Colon and Rectum", Cancer, vol. 28, (1971), No. 1, pp. 3–13; Denis P. Burkitt.

Primary Examiner—A. Lionel Clingman
Attorney, Agent, or Firm—Oblon, Spivak, McClelland, Maier & Neustadt

[57] ABSTRACT

A liquid food comprising polydextrose and oligosaccharides which are hard to digest and easy to ferment is provided. This liquid food has excellent effect for relieving constipation.

4 Claims, No Drawings

LIQUID FOOD FOR CURING CONSTIPATION: POLYDEXTROSE AND OLIGOSACCHARIDE

BACKGROUND OF THE INVENTION

This invention relates to a liquid food effective for improving constipation. Particularly, this invention relates to a liquid food effective for improving constipation, which being superior in taste, and pleasant to the palate.

Recently the role of fibrous materials contained in food, that is so called edible fibers or dietary fibers, in dietary life has become more and more important. There have already been many studies regarding the physiological importance of taking in edible fiber. For example, one of the result that Burkitt reported in "Epidemiology of Cancer of the Colon and Rectum", CANCER Vol 28(1971) No. 1, pp 3–13 after studying the dietary life of African natives, is that those people who had diets that included lot of edible fiber had lower rates of appendicitis, diverticulum diseases, cardiovascular diseases and colic cancer than Westerners with low fiber diets. Also, in "Physiochemical Characteristics and Nutritive Effectiveness of various Dietary Fiber (DF)", Proceeding, 33rd Annual Meeting of Japanese Society of Nutrition and Food Science (May 1–3, 1979, Tokyo), Ebihara et al, as a result of experiments using edible fibers and wheat bran, confirmed that edible fibers shorten retention time of food in the body, and increases the amount and water content of feces.

These results of these studies hold interest particularly from the aspect of curing and preventing constipation, and recently it is being done to treat a material abundant in edible fibers such as bran or germ for easy eating or blend into a conventional foods. Further, the use of edible fiber together with other physiologically useful substances to enhance their effects has also been tried. For example Japanese Patent Laid Open No. 59-173062 offers a health food for improving constipation which consists of edible fiber and a proliferation accelerating factor for bifidobacterium (eg. lacturose).

However, ad edible fibers are generally difficult to stably suspend in water, such a conventional kinds of foodstuffs were limited to foods in a solid state, and there has been no liquid food or beverage having incorporated edible fiber in order to improve constipation. And also, the above mentioned conventional food containing edible fiber can easily have their taste and texture corrupted by the addition of edible fiber, therefore, if taste should be taken into consideration as an important factor, there is the problem that sufficient amounts of edible fiber cannot be incorporated therein. Further, the fact that liquid food cannot be produced makes it difficult to increase the variety of presentable foods containing edible fiber, making it hard to meet consumers' diversified tastes.

In order to expect significant effect, in many cases fairly large amounts of edible fiber should be taken, but this is often accompanied by side effects such as diarrhea, flatulence, abdominal inflation, celialgia, etc. Therefore it is not recommendable to take in too much edible fiber at one time.

SUMMARY OF THE INVENTION

This invention relates to providing a novel liquid food having superior taste and texture that is easy to ingest, and which is small amounts, can impart remarkable effects in improving constipation.

A liquid food provided by the present invention comprises, as main components for improving constipation, polydextrose and oligosaccharides which are hard to digest and easy to ferment.

An example of a liquid food provided by the present invention comprises, as main components for improving constipation, polydextrose and raffinose family oligosaccharides which are made from soybean and are hard to digest and easy to ferment.

Another example of a liquid food provided by the present invention comprises, as main components for improving constipation, polydextrose and galactose series oligosaccharides which are made from lactose and are hard to digest and easy to ferment.

DETAILED DESCRIPTION OF THE INVENTION

In a liquid food of the present invention, both polydextrose and oligosaccharides are completely water soluble, have no solid substance and have good texture. Although each component has an effect for improving constipation, much greater effects are shown when both components are used together.

In the present invention, liquid food refers not only to a food which is fluid in its ordinary state but also to a food having a potentially fluid character which can be easily converted to a liquid food such as pudding, jelly or ice cream when agitated or heated. In the present invention, a food also includes a beverage.

Polydextrose means water soluble polysaccharide having a molecular weight of about 1500–18000 which is obtained by polymerizing glucose or maltose in a molten state using edible carboxylic acid, eg. citric acid, as a catalyst and crosslinking agent. Apart from above-mentioned polysaccharide, there are those which are obtained by reacting polyol such as sorbitol in order to decrease viscosity and to improve color and taste, a method for making such products is described in U.S. Pat. No. 3,766,165. The molecular chain of the polysaccharide is highly branched and hard to digest and the calorific content of it as a food is as low as 1 calorie per gram, heretofore it having been used as a low calorie saccharic foodstuff. According to the inventors' confirmation, polydextrose, being different from oligosaccharides which are another component of the present invention that are hard to digest and easy to ferment, is difficult to be utilized even by intestinal bacteria. The substance is being sold by Pfizer Inc. under the trade name of "Polydextrose".

On the other hand, oligosaccharides, which are hard to digest and easy to ferment, are difficult for digesting enzymes secreted from the human digestive tract to digest but they are easily utilized by intestinal bacteria. For example, the oligosaccharides of the invention are such fermentable substances that when mixed with four time diluted fresh human feces and kept in an anaerobic condition, more than 90% would be diminished. In ordinary terms oligosaccharides include disaccharides, however, as most disaccharides are easy to digest and those disaccharides that are not easy to digest do not show significant effect when used together with polydextrose, disaccharides are excluded from the oligosaccharides of the present invention.

Especially preferable oligosaccharides for the present invention are those which can be utilized by bifidobacteria having a regulatory effect on intestine. The oligosaccharides exemplified are: such raffinose family oligosaccharides which are made from soybean having the structure Gal—(Gal)$_n$—Glc—Fru, n=0, 1, where Gal is a galactose moiety, Glc is a glucose moiety and Fru is a fructose moiety described in Japanese Patent Laid Open No. 59-179064, galactose series oligosaccharides which are made from lactose having the structure Gal—(Gal)$_m$—Glc m=1-4 described in Japanese Patent Publication No. 58-20266, (corresponding to U.S. Pat. No. 4,435,389) fructooligosaccharides having the structures Fru—(Fru)$_m$—Glc m=1-4 or Fru—(Fru)$_n$—Glc—Fru n=0, 1 described in Japanese Patent Publication No. 59-53834, product of decomposition of Konjak mannan which is an oligosaccharide comprised of glucose and mannose, described in Japanese Patent Laid Open No. 58-212780, levan (beta-2,6-fructan) having the structure Fru—($\beta$-2,6)-[Fru—($\beta$-2,6)]$_p$-Fru p=1-28 described in Japanese Patent Laid Open No. 57-18982, galactose series oligosaccharides which are made from lactose having the structure Gal—(GlcNAc)$_m$—Glc, m=1-4 where GlCNAc is an N-acetylglucosamide moiety described in Japanese Patent Laid Open No. 58-99497, partially hydrolyzed chitin having the structure Gal—Glc—Fru described in Japanese Patent Laid Open No. 59-11190, lactosucrose having the structure Gal—($\beta$-1,6)—Glu—($\beta$-1,4)Gal described in Japanese Patent Publication No. 59-53835.

Mixing ratio of polydextrose and oligosaccharides which are hard to digest and easy to ferment is suitably about 1:10-20:1. A liquid food of the present invention can be incorporated, apart from polydextrose and oligosaccharides which are hard to digest and easy to ferment, with other oligosaccharides which are hard to digest and are water soluble or water dispersible, seasonings, flavors, and other appropriate materials in so far as they do not adversely affect the achievement of the present invention. Especially, lactobacilli, streptococci, bifidobacteria or fermented milk containing them which have a regulatory effect on intestine preferable as subcomponents, since they are superior in view of their ingestive effect in the liquid food of the present invention.

In the present invention, both polydextrose and oligosaccharides are also effective in improving constipation. Although the mechanisms which affect said improvement are not clear, it is deemed that they both work in different ways due to their different fermenting abilities in the intestines, and when they are used together, significant effects much more superior to their being used along can be shown. Since both materials are completely water soluble, they are suitable for making a liquid food having no solid residue and good texture.

Since the liquid food of the present invention achieves the object of improving constipation through the use of water soluble polydextrose and oligosaccharides, it has a taste and texture superior to those of conventional health foods which contain solid edible fibers. Moreover, since it is s stable liquid, it can be made in a variety of forms such as a beverage, fermented milk, jelly, ice cream etc., and can meet diversified consumers' tastes.

EXAMPLE

In order to explain the invention in more detail, dosage tests and manufacturing examples are shown below.

In each example the polydextrose used was manufactured by Pfizer Inc.

Dosage Tests

The effects on constipation of polydextrose and raffinose family oligosaccharides which were made from soybean were inspected by dosing them solely respectively or all together at the same time to subjects comprising an adult male and nine adult females complaining of constipation or a touch of constipation. The raffinose family oligosaccharides used were prepared by a method described in Japanese Patent Laid Open No. 59-179064, where soybean whey was treated with calcium hydroxide.

Amount of Dose

| test group 1: | polydextrose | 10 g/day |
|---|---|---|
| test group 2: | raffinose family oligosaccharides | 3 g/day |
| test group 3: | polydextrose and | 5 g/day |
| | raffinose family oligosaccharides | 3 g/day |

Duration of Dose

Each test group was dosed for 2 weeks. In order to avoid any influences from a preceding test, a non dosage term of one week was set between each test group. Testing order for the groups was randomly changed according to subjects.

Method of Inspecting the Results

All subjects were requested to fill out and respond to a questionare containing the following items everyday before, in the midst of, and after each dosage:
1. Whether defecation had occured;
2. Ease in defecating;
3. Amount of stool (great, normal, little);
4. Nature of stool (hard, medium, soft, diarrhetic);
5. Feeling after defecation (feeling of relief or not);

Method for Analyzing the Results

The results were scored as follows:
1. Frequency of defecation;
   frequency of defecation/test term (14 days)
2. Ease of defecation;
   frequency of easy defecation during test term/frequency of defecation during test term
3. Amount of stool;
   Points of 3, 2, and 1 were allotted for the amount ie. great, normal, little, respectively and totaled through the duration of the dosage.
4. Hardness;
   Points of 1, 2, 3, and 4, were allotted for the hardness ie. hard, medium, soft, and diarrhetic, respectively.
   Total points were divided by the frequency of defecation with the quotient as the resulting score.
5. Degree of relief;
   frequency the subject felt sense of relief after defacation/frequency of the defecation made during the test The resulting score are shown in Table 1 and Table 2 hereinbelow.

Table 1 shows the results of effect for improving constipation according to each test group, where a circle expresses that four or more than four items out of the five items tested had improved compared to before the dosage. Table 2 shows the items which were judged as showing significantly increased scores according to "Student's t-test" for each item comparing the state before dosage and the result of the test.

TABLE 1

| subject | test group 1 | test group 2 | test group 3 |
|---|---|---|---|
| A | O | O | O |
| B |   |   | O |
| C | O |   | O |
| D |   | O |   |
| E |   |   |   |
| F |   |   |   |
| G | O | O | O |
| H |   | O | O |
| I | O |   |   |
| J |   |   | O |
| number of subjects scoring as effective | 4 | 4 | 6 |

TABLE 2

| test group | items showing significantly increased score |
|---|---|
| 1 | none |
| 2 | frequency of defecation and amount. |
| 3 | frequency of defecation, amount, ease and hardness. |

In general, a condition where constipation is cured can be seen as a condition where freqency of defecation is increased, feces becomes soft and easy to deject, and where the subject feels relieved after defecation. Hence, it cannot be determined that constipation is cured after seeing an improvement in only one item. Therefore the indispensable requirements for judging whether constipation has been cured are as follows:

(1) With respect to one item, the score increases significantly through all subjects;
(2) Through all subjects, a significant increase in score can be seen in as many items as possible;
(3) With respect to an individual subject, the scores increase in almost all items.

In determining the above results based on the three items above, a curing effect on constipation cannot be seen at all when only polydextrose was dosed, a slightly effect can be seen with oligosaccharides alone, and can be strongly recognized when polydextrose and oligosaccharides are used together.

MANUFACTURING EXAMPLES

Example 1

To 10 liters of apple juice, 500 g of polydextrose and 300 g of raffinose family oligosaccharides which were made from soybean as used in the above test were added and sterilized by heating to 100° C. for 30 minutes. The thus obtained fruit juice was clear, having good taste and flavor with no odd sensations to the palate.

Example 2

To 100 parts by weight of commercial fermented milk product containing bifidobacterium (produced by KK Yakult Honsha and sold under the trade name of "MIL-MIL"), 5 parts by weight of polydextrose and 3 parts by weight of galactose series oligosaccharides which were produced from lactose according to a method described in Japanese Patent Publication No. 58-20266 were added in an aseptic condition. The beverage obtained was not inferior to the fermented milk used as a raw material with respect to taste and pleasant feeling to the palate.

Example 3

To 400 g of polydextrose, 240 g of raffinose family oligosaccharides as used in the previous example, 24 g of citric acid and 670 g of sucrose, water was added to make 10 liters of liquid, and sterilized by heating to 100° C., for 30 minutes. To the resulting mixture was added 1 liter of fermented milk which was previously prepared by culturing Lactobacillus casei on a culture medium of 10% skimmed milk, and having $1 \times 10^9$/ml of viable cells. The lactobacilli-containing beverage thus obtained had good taste and flavor and a pleasant feeling to the palate.

Example 4

Using the following recipe, ice cream was made according to a conventional method:

| | |
|---|---|
| raw cream (45% formulated) | 1000 g |
| milk | 450 |
| polydextrose | 75 |
| 55% fructo-oligosaccharides syrup* | 118 |
| sugar | 100 |
| egg yolks | 200 |
| flavor | a few drops |

*produced by Meiji Seika KK, Bx 73.5

The product thus obtained was not any different from conventional ice cream in pleasant feeling to the palate.

Example 5

With the following recipe, coffee jelly was made according to a conventional method.

| | |
|---|---|
| instant coffee powder | 25 g |
| polydextrose | 100 |
| 50% galactose series oligosaccharides | 172 |
| sugar | 75 |
| water | 1000 |
| gelatine | 25 |

*made by a method according to Japanese Patent Laid Open No.58-20266, Bx 70

The product thus obtained was not any different in texture from conventional coffee jelly.

What we claim is:

1. A liquid food, which is helpful in correcting constipation, comprising:
   (a) a water soluble polysaccharide composed of glucose or maltose units having a molecular weight of 1,500 to 18,000 and
   (b) an oligosaccharide of at least 3 saccharide units which is utilizable by intestinal bifidobacteria selected from the group consisting of:
      (i) raffinose family oligosaccharide: Gal—(Gal)$_n$—Glc—Fru, n=0, 1;
      (ii) galactose series oligosaccharide:
         Gal—(Gal)$_m$—Glc, m=1, 2, 3, 4
         or Gal—($\beta$-1,6)—Glc—($\beta$-1,4)—Gal;
      (iii) fructooligosaccharide:
         Fru—(Fru)$_m$—Glc, m=1, 2, 3, 4
         or Fru—(Fru)$_n$—Glc—Fru, n=0, 1;

(iv) decomposition product of Konjak mannan which is an oligosaccharide comprised of glucose and mannose;

(v) levan ($\beta$-2,6-fructan):
Fru—($\beta$-2,6)—(Fru—($\beta$-2,6))$_p$=Fru; p=1–28;

(vi) partially hydrolyzed chitin:
Gal—(GlcNAc)$_m$—Glc, m=1, 2, 3, 4; and (vii) lactosucrose: Gal—Glc—Fru, where Gal=galactose moiety, Glc=glucose moiety, Fru=fructose moiety, GlcNAc=N-acetylglucosamine moiety, and wherein (a) and (b) are admixed in a ratio of about 1:10 to about 20:1.

2. A liquid food according to claim 1, characterized in that the oligosaccharides are raffinose and/or stachyose oligosaccharides which are made from soybean.

3. A liquid food according to claim 1, characterized in that the oligosaccharides are galactose series oligosaccharides which are made from lactose.

4. A liquid food according to claim 1, characterized in that the liquid food is a beverage.

* * * * *